United States Patent [19]
Jacobson et al.

[11] Patent Number: 5,564,430
[45] Date of Patent: Oct. 15, 1996

[54] AUTOMATIC CONTROL OF THE SENSING THRESHOLD FOR MONITORING CARDIAC RHYTHM IN A IMPLANTABLE DEVICE

[75] Inventors: Peter Jacobson, Haguenau; Daniel Kroiss, Schweighouse-Moder, both of France

[73] Assignee: Ela Medical S.A., Le Plessis-Robinson Cedex, France

[21] Appl. No.: 340,624

[22] Filed: Nov. 16, 1994

[30] Foreign Application Priority Data

Nov. 17, 1993 [FR] France .................................. 93 13733

[51] Int. Cl.⁶ .................................................. A61B 5/0456
[52] U.S. Cl. ............................ 128/697; 128/708; 128/901
[58] Field of Search ................................. 128/696, 697, 128/704, 705, 708, 901, 902; 607/9, 5, 28, 27; 364/413.06

[56] References Cited

U.S. PATENT DOCUMENTS

| | | |
|---|---|---|
| 4,184,493 | 1/1980 | Langer et al. . |
| 4,393,877 | 7/1983 | Imran et al. ........................... 128/705 |
| 4,559,946 | 12/1985 | Mower . |
| 4,708,144 | 11/1987 | Hamilton et al. ................... 128/696 X |
| 4,779,617 | 10/1988 | Whigham ............................ 128/696 X |
| 4,819,643 | 4/1989 | Menken . |
| 4,880,004 | 11/1989 | Baker, Jr. et al. . |
| 4,940,054 | 7/1990 | Grevis et al. . |
| 4,967,747 | 11/1990 | Carroll et al. . |
| 5,048,535 | 9/1991 | Maruyama ............................. 128/708 |
| 5,050,599 | 9/1991 | Hoegnelid . |
| 5,117,824 | 6/1992 | Keimel et al. . |
| 5,339,820 | 8/1994 | Henry et al. . |
| 5,365,932 | 11/1994 | Greenhut ................................ 128/696 |

FOREIGN PATENT DOCUMENTS

| | | | |
|---|---|---|---|
| 0334618 | 9/1989 | European Pat. Off. ....... | A61N 1/365 |
| 0399059 | 11/1990 | European Pat. Off. ......... | A61N 1/36 |
| 0429025 | 5/1991 | European Pat. Off. ......... | A61N 1/08 |
| 0549438 | 6/1993 | European Pat. Off. ......... | A61N 1/08 |
| 2195538 | 4/1988 | United Kingdom ........... | A61N 1/365 |

*Primary Examiner*—William E. Kamm
*Assistant Examiner*—Jeffrey R. Jastrzab
*Attorney, Agent, or Firm*—Orrick, Herrington & Sutcliffe

[57] ABSTRACT

An improved automatic sensing threshold control for cardiac rhythm detection in an implantable device. The improvement includes setting the sensing threshold according to the amplitude of both sensed signals corresponding to cardiac activity and sensed noise, for setting the threshold substantially below the sensed signal amplitude, but above the noise amplitude. The invention provides absolute refractory periods after pacing or sensing, followed by a retriggerable noise refractory period. Following sensing the device sets the sensing threshold to approximately one-fourth of the measured amplitude, and then increases the threshold when it detects noise.

36 Claims, 3 Drawing Sheets

AUTOMATIC CONTROL OF THE SENSING THRESHOLD FOR MONITORING CARDIAC RHYTHM IN A IMPLANTABLE DEVICE

FIELD OF THE INVENTION

This invention relates to sensing cardiac signals, and more particularly to control of sensing circuits that automatically adjust their sensitivity, and logic control therefor, for implantable cardiac monitoring devices, such as tachyarrhythmia detectors and cardiac stimulation devices using direct heart electrodes.

BACKGROUND OF THE INVENTION

The present invention will be described in the context of an implantable cardiac control device such as a defibrillator or cardioverter for processing tachycardia and tachyarrythmia events, but it can also be applied to cardiac stimulation devices (also known as pacemakers) for processing bradycardia events, which two kinds of devices are often combined in a single implanted machine (often referred to as an antitachycardia pacemaker). More particularly, the present invention concerns circuits and methods for detecting the occurrence of a cardiac depolarization in the tissue adjacent to one or more electrodes in contact with or in proximity to the heart, to provide for the determination and analysis of the cardiac rhythm.

Circuits for detecting cardiac signals, which have an automatic adjustment of the sensitivity threshold for detecting the signals, are known. As used herein, the terms "sensing threshold", "detection threshold", and "sensitivity threshold" are used interchangeably to indicate the threshold amplitude above which a signal coupled from the heart, under the conditions described herein, is determined to be a "sensed signal". The terms "sensed signal" and "detection" are used interchangeably to refer to a signal corresponding to a cardiac depolarization complex.

A problem with these known circuits is that the sensitivity threshold is automatically set either too low to avoid detection of noise or other spurious interference signals, or too high to detect certain cardiac depolarizations, and not at a level that adequately rejects noise and ensures detection of cardiac depolarizations. Several of the known prior art techniques addressing this problem are as follows.

Langer U.S. Pat. No. 4,184,493 (filed February 1978) refers to a sensing circuit for an implantable defibrillator, having an amplifier, a first-order high-pass filter (the corner frequency of which is undisclosed), a bidirectional comparator, and a circuit which measures the fraction of time that the comparator asserts its output. The detector ultimately measures the average fraction of time that the ECG signal has a high slope compared to the time it has a low slope The circuit provides feedback to adjust amplifier gain automatically to maintain constant amplitude at filter output.

Imran U.S. Pat. No. 4,393,877 (filed May 1981) refers to a sensing circuit for an implantable defibrillator, which includes a slew rate detector circuit and a zero-crossing detector circuit. The slew rate detector has an amplifier, a first-order high-pass filter (corner frequency undisclosed), a unidirectional comparator, and a monostable multivibrator for timing a refractory period. The Imran circuit provides feedback to adjust amplifier gain automatically to maintain constant amplitude at filter input.

Mower U.S. Pat. No. 4,559,946 (filed June 1982) also refers to a sensing circuit synchronizing shocks to cardiac activity in an implantable defibrillator, which includes a slew rate sensitive circuit followed by a comparator. The Mower circuit provides feedback to adjust the comparator threshold automatically to a fraction of recent peak filter output.

Menken U.S. Pat. No. 4,819,643 (filed November 1986) discloses a defibrillator with pacing and sensing functions, and a separate fibrillation sensing channel with automatic gain control, which retards pacing (stimulation) until the fibrillation sensing channel gain reaches maximum sensitivity.

Grevis U.S. Pat. No. 4,940,054 (filed April 1988) refers to a defibrillator with at least two values of sensitivity, which are switched depending on the type of detected rhythm.

Baker U.S. Pat. No. 4,880,004 (filed June 1988)refers to a sensing circuit for arrhythmia detection, which includes an input amplifier with an unspecified bandpass, followed by a sensing channel with a high-pass filter at 25 Hz, and a measuring channel with additional high-pass filtering at 12 Hz, each channel followed by comparators. The Baker circuit provides feedback to adjust amplifier gain automatically to maintain constant sensing margin (the amount by which the signal in the sensing channel exceeds its threshold). Due to the additional filtering in the measuring channel this margin improves at low frequencies.

Carroll U.S. Pat. No. 4967747 (filed May 89) refers to an implantable defibrillator with a sensing circuit, consisting of a switched capacitor gain/filter block with unspecified bandpass, designed to provide glitch-free (smooth) gain changes for automatic gain control.

Keimel U.S. Pat. No. 5,117,824 (filed November 1990) refers to an implantable pacing and sensing circuit with automatic threshold control, which does not adjust the threshold after pacing, and which sets threshold according to measured amplitude after sensing, gradually reducing threshold thereafter.

The question of adjusting the sensitivity, particularly for defibrillators and cardioverters (but not exclusively) has not resulted in a satisfactory solution and remains the subject to a number of controversies.

In "State-of-the-Art of the AICD", Pace May 1991 Winkle described a defibrillator without automatic gain control, for which "programming sensitivity requires great care at time of implantation and during follow-up to be certain that T waves are not oversensed and most importantly that ventricular fibrillation/tachycardia is not undersensed".

In "Failure of a Second and Third Generation Implantable Cardioverter to Sense Ventricular Tachycardia: Implications for Fixed-Gain Sensing Devices", Pace, May 1992, Sperry et al. wrote that "more sensitive fixed-gain settings or automatic-gain sensing are needed to detect low amplitude signals on a consistent basis. The undesirable aspect of using such high sensitivity is that of oversensing (e.g., T waves) by the device resulting in an increased risk of inappropriate discharges. Failure to sense ventricular fibrillation has however also been reported with automatic gain devices as well".

SUMMARY OF THE INVENTION

It is thus apparent that a sensing circuit for a tachyarrhythmia detector needs to detect cardiac depolarizations but reject undesired signals, including cardiac repolarization (T wave), and including signals emanating from the return to equilibrium of the electrode system and the pacemaker's output circuit after pacing, called pacing artifact. Prior art techniques use high pass filters, refractory periods, and automatic gain or detection threshold control. Prior art tachyarrhythmia detectors only take into account measured signal amplitude, for setting sensitivity. This invention provides an improved automatic sensitivity threshold control which takes into account both signal and noise amplitude to optimize sensitivity.

It is, therefore, an object of this invention to provide a sensing threshold which depends on the amplitude of both sensed signal and sensed noise, to adjust and optimize the sensitivity for setting the sensitivity threshold substantially below the sensed signal amplitude, but above the noise amplitude and other sources of interference.

It is a further object of this invention to provide automatically a sensitivity threshold that is set equal to a predetermined value after pacing, and to increase this set sensitivity threshold above the amplitude of noise detected after pacing. The predetermined value may be set by external programming and stored in a memory of the device.

It is still another object of the invention to avoid changing the sensitivity threshold when single cardiac events cause detections occurring after the end of an absolute refractory period following pacing (stimulation) or sensing (detection of a spontaneous cardiac depolarization).

Broadly, the present invention concerns a method for automatically adjusting the sensitivity of a circuit for detecting cardiac rhythm in which both the sensed cardiac signal amplitude and the sensed noise are used to select the detection threshold. One aspect of the invention is directed to a method for automatically adjusting the sensing threshold in a cardiac rhythm detecting device. One such method includes the steps of:

measuring the filtered amplitude of a sensed signal corresponding to cardiac activity, setting the sensing threshold to a predetermined fraction of said measured amplitude, timing an absolute refractory period following said sensed signal (i.e., the cardiac activity), timing a noise refractory period following said absolute refractory period, restarting said noise refractory period upon the detection of a sensed signal corresponding to cardiac activity exceeding said set sensing threshold during said noise refractory period, and incrementing said sensing threshold upon said detection in said noise refractory period, for increasing the sensing threshold above the noise amplitude.

Preferably, after delivery of a pacing pulse the following additional steps are applied:

setting the sensing threshold to a predetermined value, timing an absolute refractory period following said paced activity, timing a noise refractory period following said absolute refractory period, restarting said noise refractory period upon the detection of a sensed signal corresponding to cardiac activity exceeding said set sensing threshold during said noise refractory period, and incrementing said sensing threshold upon said detection in said noise refractory period, for increasing the sensing threshold above the noise amplitude.

The predetermined fraction of measured amplitude preferably falls between one-eighth and one-half, and more preferably is one-fourth. Further, the step of setting the sensing threshold to a predetermined fraction of said measured amplitude may include the additional step of limiting said sensing threshold between predetermined minimum and maximum values, for example between approximately 0.4 mV and approximately 1.6 mV.

In one preferred embodiment, the foregoing method includes the additional step of disabling said incrementing step until the noise refractory period has been restarted a predetermined number of times, or until a predetermined time has elapsed since the end of the absolute refractory period.

In addition, the sensing threshold may be incremented at the end (timeout) of the noise refractory period, when the noise refractory period has been restarted a predetermined number of times. Incrementing the sensing threshold upon any of the aforementioned conditions, is preferably by a uniform increment of e.g., approximately 0.2 mV. The duration of the noise refractory period typically ranges from 30 to 100 ms, and is preferably 31 ms. The noise refractory period is also known in the art as a relative refractory period.

BRIEF DESCRIPTION OF THE DRAWINGS

Further features of the invention, its nature and various advantages, will be apparent from the accompanying drawings and the following detailed description of the invention, in which.

DETAILED DESCRIPTION OF THE INVENTION

Figure 1:
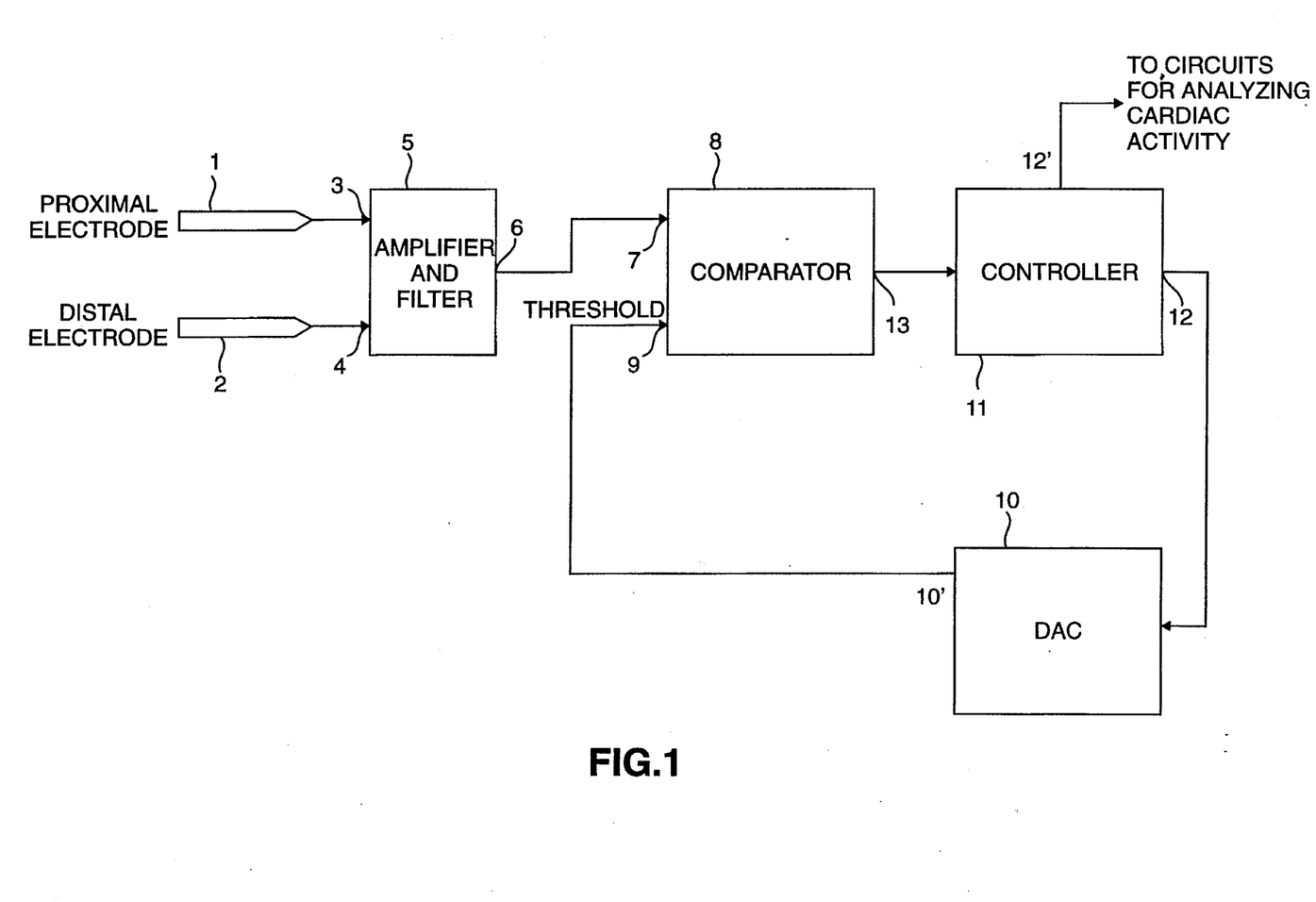
FIG. 1 shows a schematic block diagram of a sensing circuit in accordance with a preferred embodiment of the invention.

Referring to FIG. 1, a sensing circuit for a tachyarrhythmia detector according to the invention is shown. A bipolar direct heart electrode pair, having a proximal terminal 1 and a distal terminal 2, couples the cardiac signal to the differential inputs 3, 4 of a circuit 5 for conditioning the signal by amplification and filtering (hereinafter called "filter 5"). In the preferred embodiment of the invention, the filter 5 provides a third-order high-pass characteristic with corner frequency at approximately 16 Hz, at least a first-order low pass characteristic at approximately 100 Hz, and a mid-band gain of approximately 125. Such circuits are described in copending and commonly assigned U.S. patent application Ser. No. 08/287,843, filed Aug. 9, 1994 entitled Sensing Circuit For Tachyarrhythmia Detection, the disclosure of which is hereby incorporated herein by reference in its entirety. The filter 5 has an output 6 (also referred to as the "filtered output" or "filtered amplitude") which connects to one input 7 of a comparator 8. The other input 9 of comparator 8 connects to a reference voltage, the so-called the sensing threshold, provided in the preferred embodiment by the output 10' of a digital to analog converter 10.

Referring still to FIG. 1, a controller 11 has digital output 12 to set the comparator sensing threshold at input 9 via digital to analog converter 10. Controller 11 also receives the output 13 of comparator 8, indicating when output 13 is asserted that the sensing circuit detects a cardiac depolarization. The controller 11 has an output 12' to transmit the cardiac depolarization indication to circuits, and/or software for analysis of the cardiac rhythm (not shown, but known in the art) and possible triggering of an appropriate response, e.g., stimulation, cardioversion or defibrillation. Controller 11 also can provide various functions as described below, including the management of refractory periods, and, via digital to analog converter 10, automatic sensing threshold control and/or programmable sensing threshold control.

Furthermore, controller 11 can rapidly adjust the sensing threshold 9 and observe comparator 8 output 13 while the filtered output 6 remains present. In this manner, the controller 11 can estimate the amplitude of the filtered output 6, because the comparator 8 only asserts its output 13 when its input 7 exceeds its sensing threshold input 9. The controller 11 can perform this measurement using successive approximations, or by generating a ramp of thresholds, as found in the operation of commercial analog-to-digital converters. One could also accomplish these objectives by implementing a flash converter as is known in commercial devices, namely a set of comparators each having its own threshold, and each connected to the controller so that the controller can determine which thresholds the filtered amplifier output exceeds at a given time.

Figure 2A:
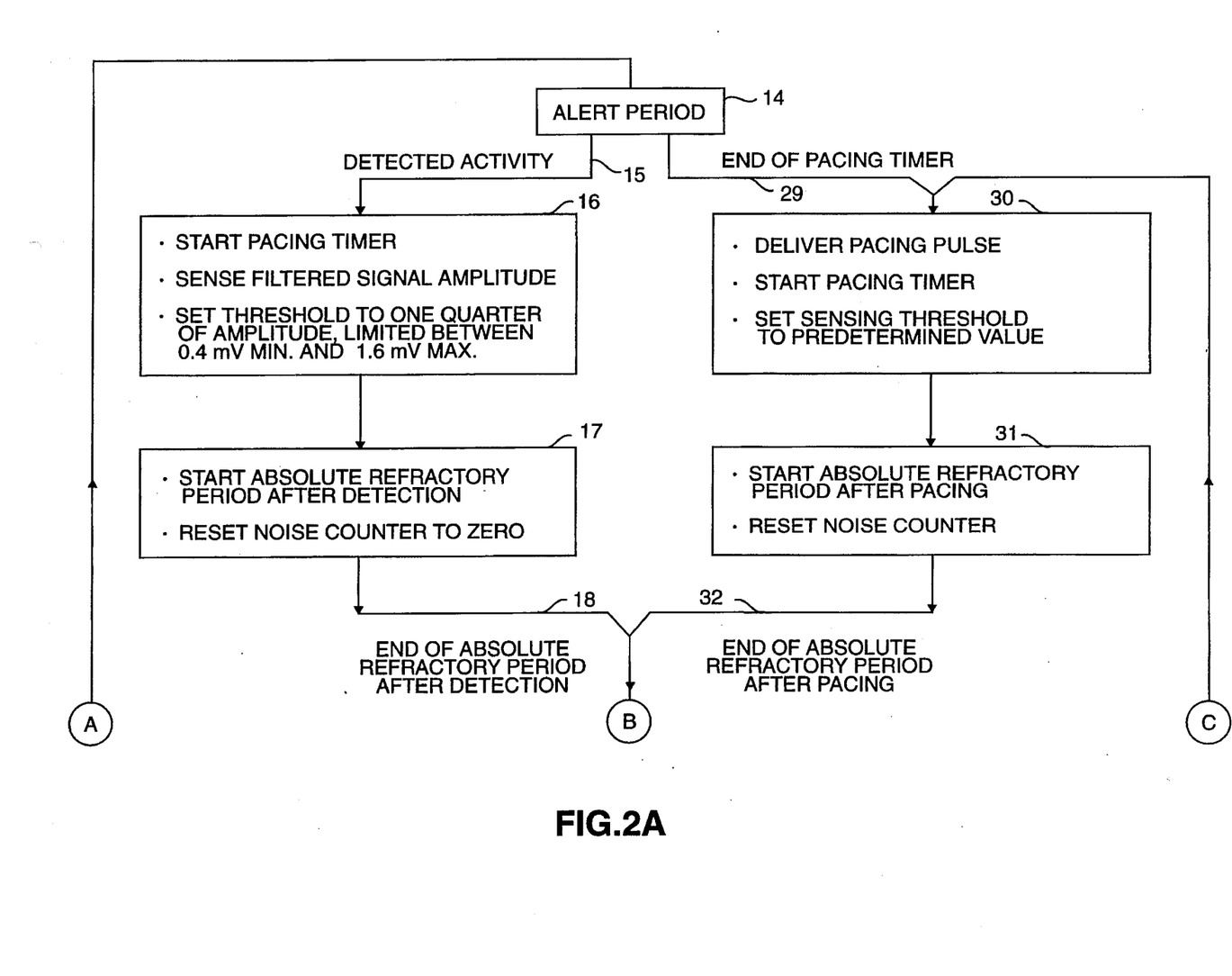
FIGS. 2A and 2B show a flowchart of a method in accordance with a preferred embodiment of the invention.
Figure 2B:
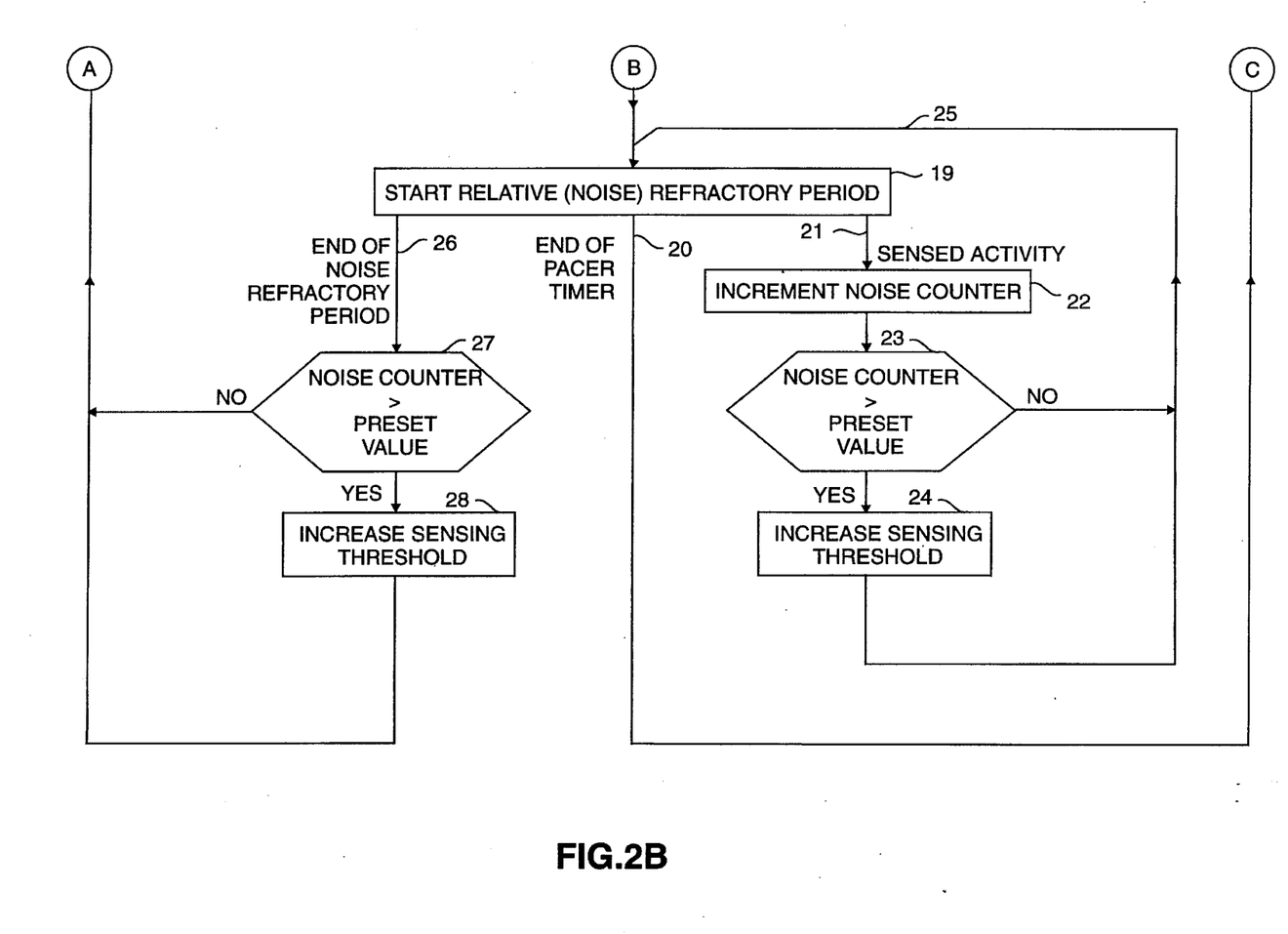

FIGS. 2A and 2B show a flowchart depicting the function of an implementation of the invention, applied in this case to a cardiac pacemaker. These functions can be implemented in hardware or software or a combination of both, following design techniques that are known to those of ordinary skill in the art. At step 14 in FIG. 2A, the device begins timing an alert period, during which it waits for sensed activity (branch 15), and at the end of which it will pace the heart if no sensed activity occurs (branch 29). This alert period is also known as the escape interval. Sensed activity is determined to occur when the filtered sensing amplifier output at 6 (FIG. 1) exceeds the sensing threshold input 9 (FIG. 1), as described above. The device uses a pacing timer to determine the end of the alert period. The timer is loaded (or restarted) after the occurrence of a pacing event, or a sensing event outside a refractory period. Pacing hardware and software exists in prior art devices and has no special significance for this invention.

Referring again to FIG. 2A, when sensed activity 15 occurs, the routine implements at step 16 the functions illustrated in FIG. 1 to measure the filtered amplitude of sensed activity as described above. Then the routine sets the sensing threshold to a predetermined fraction of that measured amplitude. In practice, good results have been obtained by setting this fraction to a value ranging between from one-eighth to one-half, with optimal performance when the fraction is set to one-fourth.

In this regard, the amplitude of cardiac signals has a wide dynamic range, varying from patient-to-patient, or even varying with time and cardiac condition in the same patient, over a range from approximately 0.4 mV to over 20 mV. For convenience, in the following discussion, sensed amplitudes and the sensing threshold refer to equivalent values at the amplifier input.

The inventors have discovered that it is advantageous to increase the sensing threshold above 0.4 mV when sensed amplitude exceeds a few millivolts, to avoid multiple detections of the same event. The inventors further have discovered that making the device with a lower threshold more sensitive than approximately 0.4 mV increased susceptibility to sensing far-field events, noise, and T-waves. The inventors also have discovered that making the device less sensitive than approximately 1.6 mV causes the device to miss detecting some lower amplitude complexes which occur in ventricular fibrillation, even when the amplitude of the preceding beat exceeded this by a factor of four. Hence, according to the invention, the routine sets the sensing threshold to one-quarter of the amplitude of the last sensed beat. However, if this would result in a threshold less than 0.4 mV, the routine sets it to 0.4 mV. Similarly, if the predetermined fraction would result in a threshold greater than 1.6 mV, the routine sets it to 1.6 mV.

At step 17, the routine begins to time an absolute refractory period after sensing. This period serves to avoid multiple detections of the same event. The controller (shown at 11 in FIG. 1) remains unaffected by cardiac activity during the absolute refractory period, which duration is typically approximately 94 ms and is programmable. Also at step 17, before, during, or after this absolute refractory period, the routine resets a counter called the noise counter to zero counts. The description below explains the use of this counter. At the end of the absolute refractory period, at step 18 (FIG. 2A) the routine begins to time a noise refractory period at step 19 (FIG. 2B). The noise refractory period also may be adjusted by external programming.

During each noise refractory period, the controller 11 can again sense events, but considers these events as noise, and thus does not affect the timing of the delivery of the next pacing pulse in response to detected events in the noise refractory period. Instead, it restarts the noise refractory period upon the detection. In this manner, continuous noise with period less than the predetermined duration of the noise refractory period will continue to fall in the noise refractory period, until the pacing timer (i.e., the escape interval started at step 16 in response to the preceding paced or sensed event) times out at step 20, causing the device to pace the heart. In an alternative embodiment, the routine can skip pacing the heart in any cycle where the device continues to find noise at the moment where it should pace, to avoid competing with an intrinsic cardiac rhythm that may be masked by the noise.

Thus, when sensed activity occurs (branch 21) during the noise refractory period, the routine considers this as noise. It increments a noise counter at step 22 each time it senses in the noise refractory period. At step 23, when this counter exceeds a predetermined value, preferably 4 counts of noise, then the device increments the sensing threshold at step 24. Typically, the increase is 0.2 mV. In this manner, more than a predetermined number of noise detections causes the sensing threshold to increase, until the device no longer senses the noise, or until the sensing threshold reaches some maximum value at which the device no longer senses anything, because this value exceeds the dynamic range of the sensing comparator.

Every time the routine senses noise, it returns at branch 25 to step 19 to restart the noise refractory period. Thus the noise refractory period will end either when the time has come to pace, shown at branch 20 in FIG. 2B, or when the device has detected nothing for at least the predetermined length of the noise refractory period, causing the noise refractory timer to time out at branch 26. Upon timeout, if the noise counter exceeds a predetermined value at step 27, this means that the device detected a certain number of counts of noise. In this case the device further increments the sensing threshold at step 28, to be sure that the sensing threshold exceeds noise amplitude by some minimum amount, before continuing to time the alert period until pacing, at step 14. Typically an increment at step 28 of 0.2 mV suffices to prevent further sensing of noise in the same cardiac cycle.

The noise counter incremented in step 22 serves to prevent increasing the sensing threshold if a single cardiac event happens to have an unusually long duration, so that the device continues to detect the event even after the end of the absolute refractory period. The use of the noise counter remains optional in the implementation of the invention, for in many patients, depending on the amplifier bandpass and the length of the absolute refractory period, the bandpass and absolute refractory period may by themselves suffice to prevent events from detection outside the absolute refractory period. For the bandpass and absolute refractory periods suggested in the preferred embodiment, the inventors have found it useful to increment the sensing threshold at steps 24 and 28 only when the noise counter exceeds approximately four counts. In other words, the routine waits four detections of noise before modifying the sensitivity threshold. This allows for not modifying the sensitivity threshold in cases where the signals continue for a time longer than the absolute refractory period, which is the case when a T wave is detected after a ventricular stimulation, but also for a spontaneous complex that continues for a period longer than the absolute refractory period, or following one of a baseline rhythm or a very rapid rhythm having RR intervals with the second R wave occurring at the end of the absolute refractory period or at the end of the noise refractory period. If, nevertheless, the signal was noise, the sensitivity threshold will then be automatically readjusted to a value above the measured amplitude because such a signal otherwise would prolong the noise refractory period.

In an alternative embodiment, the device could increment the sensing threshold only for signals detected in the noise refractory period, but occurring after at least some predetermined time following the end of the absolute refractory period. This would serve the same function as the noise counter, preventing any adjustment of sensing threshold for redetection of a single heartbeat over a time exceeding the length of the absolute refractory period. This alternative embodiment would replace the question at step 27 by a question such as: "has device sensed after a predetermined time following the end of the absolute refractory period?"

Returning now to the alert period at step 14 in FIG. 2A, if no sensing occurs and the pacing timer times out (branch 29), a stimulation pulse is delivered and the device sets the sensing threshold to a predetermined value at step 30, and starts timing an absolute refractory period at step 31. The length of the absolute refractory period after pacing may exceed considerably the length of the corresponding absolute refractory period after sensing (step 17), to insure that the device does not sense the artifact of pacing. Typically the paced absolute refractory period exceeds 175 ms. In step 31 the device also resets the noise counter count to zero. At the end of the absolute refractory period after pacing (branch 32), the device behaves as it did at the end of absolute refractory after sensing at branch 18, described above.

The predetermined length chosen for the noise refractory period represents a compromise between the minimum frequency detected as noise (which equals the reciprocal of the length of the noise refractory period) and the maximum frequency detected as signal (which equals half the reciprocal of the sum of the lengths of the absolute and noise refractory periods). Stated otherwise, the duration of the noise refractory period results from the maximum period of noise detected, to which it is set equal. The choice results from a compromise as between the maximal period for detecting fibrillation and the absolute refractory period. In this regard, to ensure the detection of fibrillation of ventricular events whose period is between the period for detecting fibrillation and the period for detecting noise, it is necessary that the sum of the absolute refractory period and the noise refractory period be less than or equal to one half of the period for detecting fibrillation. For example, if the minimum period programmed to detect fibrillation is 250 ms and the total refractory period is 125 ms, then any rhythm detected having a period below 250 ms and above the noise refractory period will be considered fibrillation.

It has been found that 31 ms is a good compromise for the length of the noise refractory period, although values up to 100 ms could operate correctly in some patients. These longer values would aid in detection of lower frequency noise sources, such as the German national railroad, which operates at 17 Hz.

This disclosure does not give details of the implementation of sensing amplifier hardware (which can include switched-capacitor or classical linear designs) and the controller (which can consist of a microprocessor or of dedicated logic circuits). Also, such features as input protection against high energy sources such as defibrillators, or against high frequency sources such as electrosurgery, are not shown. These have no bearing on the invention and also exist commercially.

In implantable medical devices, a common practice calls for using an external programmer to address, read from, and write to memory locations in the implant. The implant uses data from some of these locations to control its operation. In this manner, the external programmer can set predetermined constants in the implant. When the disclosure and claims of this invention refer to predetermined values, this includes values adjustable by such external programming.

Although the invention has been described with reference to a particular embodiment, it is to be understood that this embodiment is merely illustrative of the application of the principles of the invention and not limiting. Numerous other modifications may be made and other arrangements may be devised without departing from the spirit and scope of the present invention.

We claim:

1. A method for automatically adjusting a sensing threshold in a cardiac rhythm detecting device, comprising the steps of:

monitoring cardiac activity as a conditioned electrical signal;

measuring an amplitude of the conditioned electrical signal corresponding to a suspected cardiac event;

setting a sensing threshold to a predetermined fraction of said measured amplitude;

starting a first absolute refractory period following said sensed activity;

starting a noise refractory period following said first absolute refractory period;

restarting said noise refractory period upon detecting a measured amplitude exceeding said set sensing threshold during said noise refractory period; and incrementing said set sensing threshold upon said detection of a measured amplitude in said noise refractory period.

2. The method of claim 1 wherein the step of setting the sensing threshold further comprises setting the sensing threshold to a predetermined fraction that is between one-eighth and one-half of the measured amplitude.

3. The method of claims 2 wherein the step of setting the sensing threshold further comprises setting the sensing threshold to a predetermined fraction that is between one-fourth of the measured amplitude.

4. The method of claim 2 wherein the step of setting the sensing threshold to a predetermined fraction of said measured amplitude further comprises limiting said sensing threshold to a value between predetermined minimum and maximum values.

5. The method of claim 4 where said limiting step limits the minimum threshold value to approximately 0.4 mV.

6. The method of claim 4 wherein said limiting step limits the maximum threshold value to approximately 1.6 mV.

7. The method of claim 1, further comprising:

monitoring the delivery of a pacing pulse;

setting the sensing threshold to a predetermined value in response to a detected pacing pulse delivery;

starting a second absolute refractory period following said pacing pulse delivery;

starting said noise refractory period following said second absolute refractory period;

restarting said noise refractory period upon detecting a measured amplitude exceeding said set sensing threshold during said noise refractory period; and incrementing said sensing threshold upon said detected measured amplitude occurring in said noise refractory period.

8. The method of claims 7 wherein the step of setting the sensing threshold further comprises setting the sensing threshold to a predetermined fraction that is between one-eighth and one-half of the measured amplitude.

9. The method of claim 8 wherein the step of setting the sensing threshold further comprises setting the sensing threshold to a predetermined fraction that is one-fourth of the measured amplitude.

10. The method of claim 8 wherein the step of setting the sensing threshold to a predetermined fraction of said measured amplitude further comprises limiting said sensing threshold to a value between predetermined minimum and maximum values.

11. The method of claim 10 where said limiting step limits the minimum threshold value to approximately 0.4 mV.

12. The method of claim 10 wherein said limiting step limits the maximum threshold value to approximately 1.6 mV.

13. The method of claim 1 wherein the step of incrementing said sensing threshold further comprises incrementing the sensing threshold by an increment of approximately 0.2 mV.

14. The method of claim 13, further comprising the step of disabling said incrementing step until a predetermined time has elapsed since the end of the absolute refractory period.

15. The method of claim 13, further comprising the step of disabling said incrementing step until said noise refractory period has been restarted a predetermined number of times.

16. The method of claims 1 further comprising the step of further incrementing said sensing threshold at the end of said noise refractory period, when said noise refractory period has been restarted a predetermined number of times.

17. The method of claim 16 where the step of said further incrementing further comprises incrementing the sensing threshold by an increment of approximately 0.2 mV.

18. The method of claim 1 further comprising selecting the noise refractory period to have a duration in the range of from 30 to 100 ms.

19. The method of claim 18 where selecting said duration of said noise refractory period further comprises selecting a duration of approximately 31 ms.

20. A method for automatically adjusting the sensitivity threshold of a cardiac rhythm detecting device comprising:

a) monitoring cardiac activity and providing a conditioned signal corresponding to each cardiac activity;

b) identifying sensed and paced cardiac events;
   (i) in response to a sensed cardiac event, measuring an amplitude of the conditioned cardiac signal corresponding to the sensed cardiac event and setting a sensitivity threshold to a predetermined fraction of said measured amplitude;
   (ii) in response to a paced cardiac event, setting a sensitivity threshold to a predetermined value;

d) starting an absolute refractory period having a beginning and an end in response to the identified cardiac event;

e) starting a noise refractory period having a beginning and an end at the end of the absolute refractory period;

f) detecting a measured amplitude exceeding the set sensitivity threshold prior to the end of the noise refractory period and in response thereto restarting the noise refractory period; and g) incrementing the sensitivity threshold in response to detecting a measured amplitude exceeding the set sensitivity threshold.

21. The method of claim 20 wherein step g) comprises incrementing the sensitivity threshold after restarting the noise refractory period a predetermined number of times.

22. The method of claim 21 wherein step g) comprises incrementing the sensitivity threshold at the end of the noise refractory period after the noise refractory period has been restarted a predetermined number of times.

23. The method of claim 21, wherein step c) further comprises limiting said sensing threshold between predetermined minimum and maximum values.

24. The method of claim 23 wherein the limiting step further comprises limiting the minimum threshold value to approximately 0.4 mV.

25. The method of claim 23 wherein the limiting step further comprises limiting the maximum threshold value to approximately 1.6 mV.

26. The method of claim 20 further comprising disabling the incrementing step g) until a predetermined time has passed following the end of the absolute refractory period.

27. The method of claim 20 further comprising disabling the incrementing step g) until the noise refractory period has been restarted a predetermined number of times.

28. The method of claim 20 wherein steps c) and g) further comprise the step of limiting the sensitivity threshold to a value between a predetermined minimum value and a predetermined maximum value, and wherein the incrementing step increments the sensitivity threshold by a predetermined increment.

29. The method of claim 20, wherein step d(i) further comprises setting the predetermined fraction to a fraction that is between one-eighth and one-half.

30. The method of claim 29 wherein step d(i) further comprises setting the predetermined fraction to one-fourth.

31. The method of claim 20 wherein step g) further comprises incrementing said sensing threshold by an increment of approximately 0.2 mV.

32. The method of claim 31, further comprising the step of disabling said incrementing step until a predetermined time has elapsed since the end of the absolute refractory period.

33. The method of claim 31, further comprising the step of disabling said incrementing step until said noise refractory period has been restarted a predetermined number of times.

34. The method of claim 31, wherein step g) comprises incrementing the sensing threshold at the end of said noise refractory period after the noise refractory period has been restarted a predetermined number of times.

35. The method of claim 20 further comprising selecting the noise refractory period to have a duration in the range of from 30 to 100 ms.

36. The method of claim 35 wherein selecting said duration further comprises selecting a duration of approximately 31 ms.

* * * * *

UNITED STATES PATENT AND TRADEMARK OFFICE
CERTIFICATE OF CORRECTION

PATENT NO. : 5,564,430

DATED : OCTOBER 15, 1996

INVENTOR(S) : PETER JACOBSON, ET AL.

It is certified that error appears in the above-indentified patent and that said Letters Patent is hereby corrected as shown below:

Column 2, line 41, after "P ace " insert --,--;

Column 8, line 64, delete "between".

Signed and Sealed this

Second Day of September, 1997

Attest:

BRUCE LEHMAN

Attesting Officer

Commissioner of Patents and Trademarks